US011457890B2

United States Patent
Song et al.

(10) Patent No.: US 11,457,890 B2
(45) Date of Patent: Oct. 4, 2022

(54) ULTRASOUND BLOOD FLOW IMAGING

(71) Applicant: Mayo Foundation for Medical Education and Research, Rochester, MN (US)

(72) Inventors: Pengfei Song, Rochester, MN (US); Armando Manduca, Rochester, MN (US); Shigao Chen, Rochester, MN (US); Joshua Trzasko, Rochester, MN (US)

(73) Assignee: Mayo Foundation for Medical Education and Research, Rochester, MN (US)

( * ) Notice: Subject to any disclaimer, the term of this patent is extended or adjusted under 35 U.S.C. 154(b) by 932 days.

(21) Appl. No.: 16/079,289

(22) PCT Filed: Feb. 2, 2017

(86) PCT No.: PCT/US2017/016190
§ 371 (c)(1),
(2) Date: Aug. 23, 2018

(87) PCT Pub. No.: WO2017/146886
PCT Pub. Date: Aug. 31, 2017

(65) Prior Publication Data
US 2019/0053780 A1    Feb. 21, 2019

Related U.S. Application Data

(60) Provisional application No. 62/301,294, filed on Feb. 29, 2016, provisional application No. 62/298,583, filed on Feb. 23, 2016.

(51) Int. Cl.
*A61B 8/06*    (2006.01)
*A61B 8/08*    (2006.01)
(Continued)

(52) U.S. Cl.
CPC ............. *A61B 8/06* (2013.01); *A61B 5/026* (2013.01); *A61B 8/0891* (2013.01);
(Continued)

(58) Field of Classification Search
CPC ....... G06T 7/0012; G06T 7/168; G06T 7/262; A61B 8/06; A61B 8/0891; A61B 8/5207;
(Continued)

(56) References Cited

U.S. PATENT DOCUMENTS 6,120,446 A    9/2000  Ji et al.
7,542,622 B1   6/2009  Angellini et al.
(Continued)

FOREIGN PATENT DOCUMENTS

GN    103815933 A    5/2014
WO    2008/007080 A1    1/2008

OTHER PUBLICATIONS

Demené, Charlie, Thomas Deffieux, Mathieu Pernot, Bruno-Félix Osmanski, Valérie Biran, Jean-Luc Gennisson, Lim-Anna Sieu et al. "Spatiotemporal clutter filtering of ultrafast ultrasound data highly increases Doppler and fUltrasound sensitivity." IEEE transactions on medical imaging 34, No. 11 (2015).*

(Continued)

*Primary Examiner* — Carolyn A Pehlke
(74) *Attorney, Agent, or Firm* — Quarles & Brady LLP

(57) ABSTRACT

Described here are systems and methods for imaging blood flow in a subject's vasculature, which may include small blood vessels, using ultrasound without the need for a contrast agent. A locally implemented low-rank matrix decomposition is used together with adaptive cutoff values to provide noninvasive ultrasound blood flow imaging capable of imaging the subject's vasculature with very high spatial and temporal resolution, and without the administration of contrast agents such as microbubble contrast agents.

(Continued)

Thus, in some instances the systems and methods can be used to image blood flow in small vessels and tissue microvasculature with high spatial and temporal resolution.

28 Claims, 12 Drawing Sheets

(51) Int. Cl.
    *G01S 15/89*     (2006.01)
    *G01S 7/52*     (2006.01)
    *G06T 7/00*     (2017.01)
    *A61B 5/026*     (2006.01)
    *G01S 7/00*     (2006.01)
    *G06T 5/00*     (2006.01)

(52) U.S. Cl.
    CPC .......... *A61B 8/5207* (2013.01); *A61B 8/5269* (2013.01); *G01S 7/00* (2013.01); *G01S 7/52047* (2013.01); *G01S 7/52077* (2013.01); *G01S 15/8977* (2013.01); *G01S 15/8981* (2013.01); *G06T 5/001* (2013.01); *G06T 7/0012* (2013.01)

(58) Field of Classification Search
    CPC ....... A61B 8/5269; A61B 8/52; A61B 8/5215; A61B 8/5253; G01S 7/52047; G01S 7/52077; G01S 15/8977
    See application file for complete search history.

(56) References Cited

U.S. PATENT DOCUMENTS

| | | |
|---|---|---|
| 9,232,931 B2 | 1/2016 | Kim |
| 2011/0118606 A1* | 5/2011 | Kim .................. G01S 15/8981 600/453 |
| 2011/0213250 A1 | 9/2011 | Vion et al. |
| 2012/0022372 A1 | 6/2012 | Kim |
| 2013/0182930 A1 | 7/2013 | Trzasko et al. |
| 2014/0023255 A1* | 1/2014 | Lim .................. G01B 9/02091 382/131 |
| 2014/0039320 A1 | 2/2014 | Jespersen et al. |
| 2014/0031627 A1 | 10/2014 | Koh et al. |
| 2014/0316274 A1 | 10/2014 | Koh et al. |

OTHER PUBLICATIONS

Demené, Charlie, Elodie Tiran, Lim-Anna Sieu, Antoine Bergel, Jean Luc Gennisson, Mathieu Pernot, Thomas Deffieux, Ivan Cohen, and Mickael Tanter. "4D microvascular imaging based on ultrafast Doppler tomography." Neuroimage 127 (2016): 472-483. online Nov. 2015.*

Harville, David A. "Matrix algebra from a statistician's perspective." (1998): 164-164.*

Halko, Nathan, Per-Gunnar Martinsson, and Joel A. Tropp. "Finding structure with randomness: Probabilistic algorithms for constructing approximate matrix decompositions." SIAM review 53.2 (2011): 217-288.*

Poon, Phillip K., Wei-Ren Ng, and Varun Sridharan. "Image denoising with singular value decompositon and principal component analysis." (2009).*

Rajwade et a!., "Image Denoising using the Higher Order Singular Value Decomposition." IEEE Transactions on Pattern Analysis and Machine Intelligence, Jun. 2012 (Jun. 2012), pp. 1-15.

International Search Report and Written Opinion from PCT/US17/16190, dated Apr. 21, 2017, 15 pages.

\* cited by examiner

BEFORE EQUALIZATION AFTER EQUALIZATION

ORIGINAL BLOOD FLOW SIGNAL
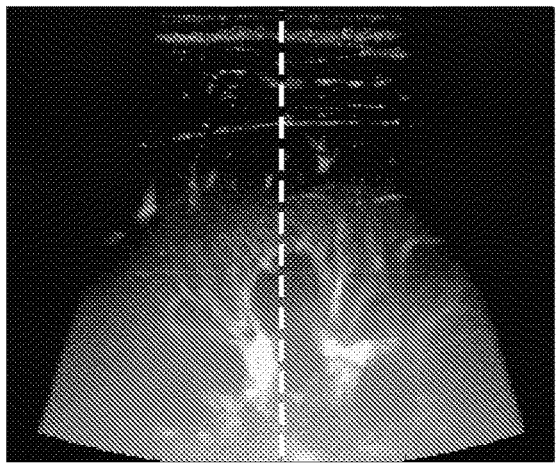
NOISE MEASUREMENT AND FITTING
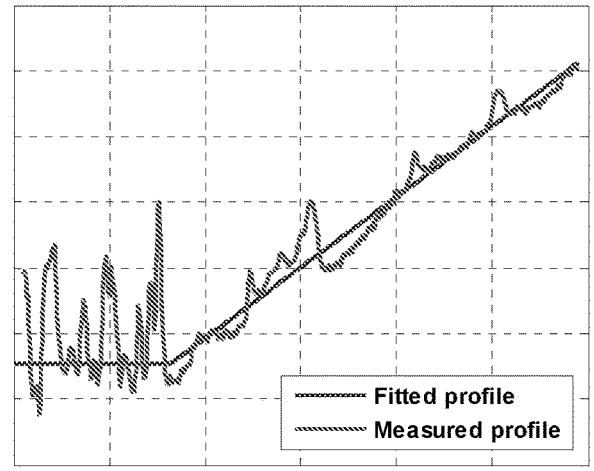
ESTIMATED NOISE FIELD
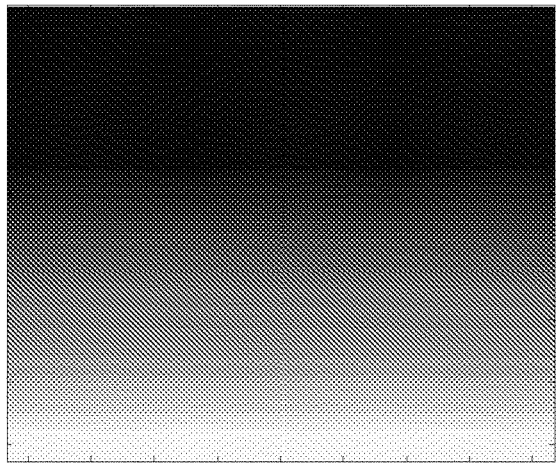
EQUALIZED BLOOD FLOW SIGNAL
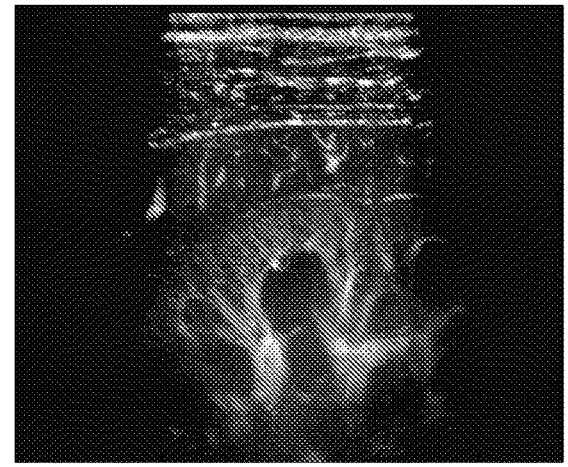
FIG. 16

ULTRASOUND BLOOD FLOW IMAGING

CROSS-REFERENCE TO RELATED APPLICATIONS

This application is a 371 U.S. National Phase Entry of PCT/US2017/016190, filed Feb. 2, 2017, which claims the benefit of U.S. Provisional Patent Application Ser. No. 62/298,583, filed on Feb. 23, 2016, and entitled "Ultrasound Small Vessel Blood Flow Imaging," and also claims the benefit of U.S. Provisional Patent Application Ser. No. 62/301,294, filed on Feb. 29, 2016, and entitled "Ultrasound Blood Flow Imaging," all of which are incorporated herein by reference in their entireties.

STATEMENT REGARDING FEDERALLY SPONSORED RESEARCH

This invention was made with government support under CIF1318347 awarded by the National Science Foundation. The government has certain rights in the invention.

BACKGROUND

The field of the present disclosure is systems and methods for imaging a subject with ultrasound. More particularly, the present disclosure relates to blood flow imaging with ultrasound.

Small vessel blood flow imaging provides critical diagnostic information for many diseases, including cancer. Angiography methods based on x-ray fluoroscopy, magnetic resonance imaging ("MRI"), and x-ray computed tomography ("CT") are the current clinical standard for small vessel imaging. However, these techniques can be invasive, have a high cost, or utilize ionizing radiation.

Contrast-enhanced ultrasound imaging ("CEUS") can also be used to image blood flow. CEUS injects microbubbles into the vessel, which provides high contrast to image small vessels. However, in addition to other technical challenges, CEUS is still considered as a semi-invasive procedure and has not been approved by Food and Drug Administration ("FDA").

Thus, there remains a need to provide a noninvasive, low cost method for imaging blood flow in small blood vessels. More generally, there also is a desire to provide blood flow imaging techniques with high spatial and temporal resolution, such as those that would be capable of imaging blood flow in small vessels, as well as in larger vasculature.

SUMMARY OF THE DISCLOSURE

The present disclosure addressed the aforementioned drawbacks by providing a method for generating an image that depicts blood flow in a subject's vasculature using an ultrasound imaging system. Ultrasound signal data are acquired from a field-of-view in a subject, and the acquired ultrasound data are divided into a plurality of ultrasound data submatrices each corresponding to a subvolume of the field-of-interest. A low-rank matrix decomposition is performed on each ultrasound data submatrix, thereby generating decomposed data that includes decomposed matrix values for each ultrasound data submatrix. At least one of a low-order cutoff value or a high-order cutoff value is estimated based on the decomposed data. The low-order cutoff value differentiates signals attributable to tissue from signals attributable to blood flow, and the high-order cutoff value differentiates signals attributable to blood flow from signal attributable to noise. Signals that are attributable to blood flow in the subject's vasculature are extracted from each ultrasound data submatrix using the at least one of the estimated low-order cutoff value or high-order cutoff value. The extracted signals are then combined to generate an image that depicts blood flow in the subject's vasculature in the field-of-view.

It is another aspect of the present disclosure to provide a method for generating an image that depicts blood flow in a subject's vasculature using an ultrasound imaging system. Ultrasound signal data is acquired from a field-of-view in a subject using the ultrasound imaging system, and a low-rank matrix decomposition is performed on the ultrasound data, thereby generating decomposed data that includes decomposed matrix values for the ultrasound data. At least one of a low-order cutoff value or a high-order cutoff value is determined based on the decomposed data. The low-order cutoff value differentiates signals attributable to tissue from signals attributable to blood flow and the high-order cutoff value differentiates signals attributable to blood flow from signal attributable to noise. Signals that are attributable to blood flow in the subject's vasculature are extracted from the ultrasound data using the at least one of the low-order cutoff value or high-order cutoff value. An image that depicts blood flow in the subject's vasculature in the field-of-view is then generated based on the extracted signals.

The foregoing and other aspects and advantages of the present disclosure will appear from the following description. In the description, reference is made to the accompanying drawings that form a part hereof, and in which there is shown by way of illustration a preferred embodiment. This embodiment does not necessarily represent the full scope of the invention, however, and reference is therefore made to the claims and herein for interpreting the scope of the invention.

BRIEF DESCRIPTION OF THE DRAWINGS

FIG. 16 illustrates an image processing-based method for noise equalization.

DETAILED DESCRIPTION

Figure 1:
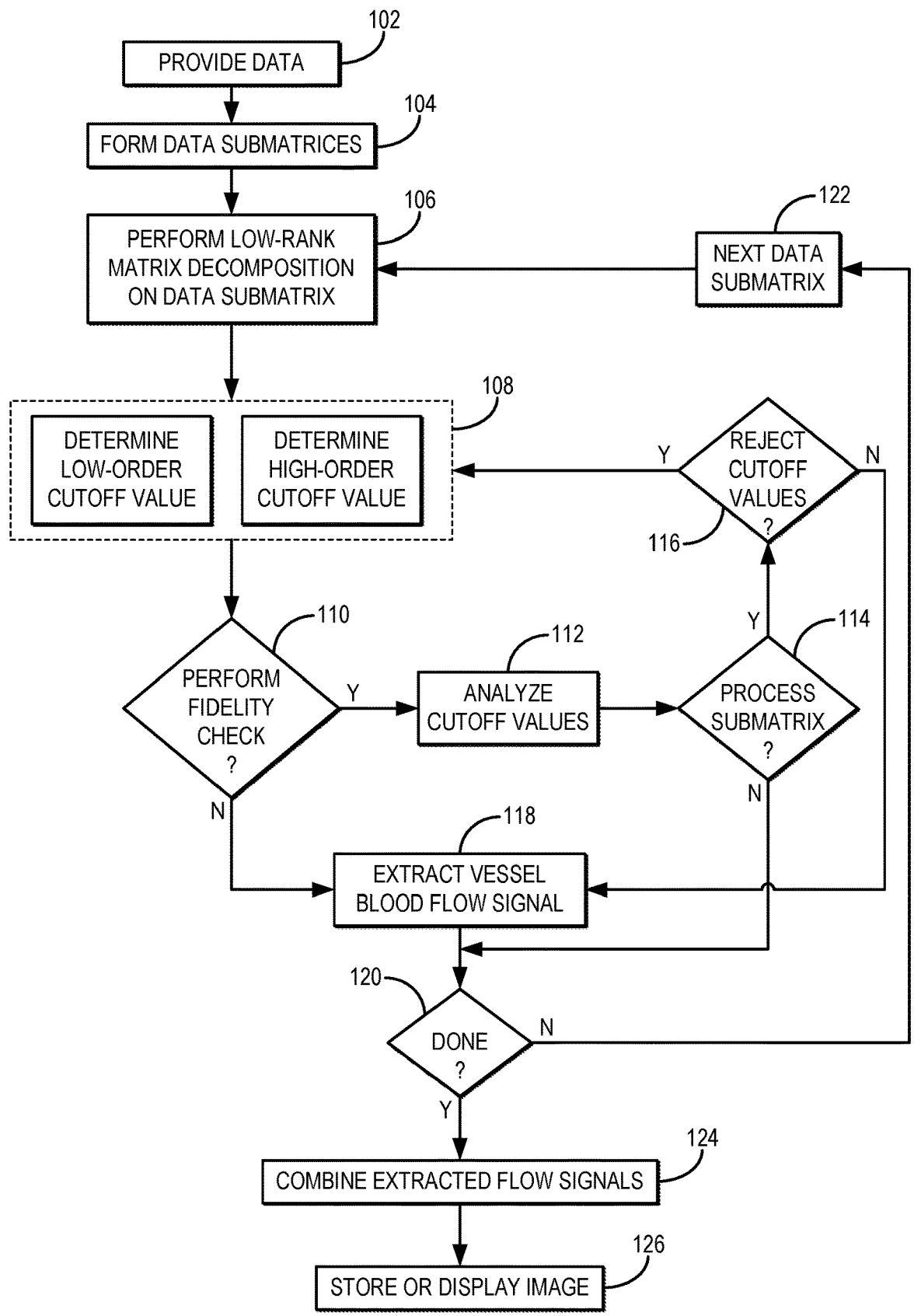
FIG. 1 is a flowchart setting forth the steps of an example method for generating an image of blood flow in a subject's vasculature, which may include small vessels, from ultrasound data using a locally adaptive low-rank matrix decomposition.

Described here are systems and methods for imaging blood flow in a subject's vasculature, which may include small blood vessels, using ultrasound without the need for a contrast agent. The systems and methods described here provide noninvasive ultrasound blood flow imaging capable of imaging a subject's vasculature with very high spatial and temporal resolution, and without the administration of contrast agents such as microbubble contrast agents. Thus, in some embodiments, the systems and methods described here are capable of imaging blood flow in small blood vessels, including tissue microvasculature; however, the systems and methods are applicable to blood flow imaging with high spatial and temporal resolution, generally.

A key challenge in ultrasound blood flow imaging is to separate the tissue signal from the blood signal. Tissue signal usually possesses much higher intensity than blood signal (e.g., about a 40 dB difference), which makes it difficult to separate the blood flow signals from the dominant tissue signal. The tissue signal is considered to be "clutter noise" in the context of blood flow imaging. However, blood flow signal behaves very differently from tissue signal in both temporal and spatial domains (e.g., the blood signal is rapidly varying with time and has a discontinuous appearance in space). This different spatial-temporal behavior of the blood signal, together with the intensity difference between tissue and blood, provides opportunities to separate the two signals.

The use of low-rank matrix decomposition techniques such as principal component analysis ("PCA") and singular value decomposition ("SVD") for clutter noise suppression in ultrasound blood flow imaging has been reported in several studies. The tissue signal typically has much higher speckle intensity and temporal coherence (i.e., slow variation along the temporal direction and the temporal variation is similar among neighboring pixels or locations) than the blood signal, and thus is typically clustered in the high singular values after SVD processing. Blood signal typically resides in the intermediate range of the singular value curve, in between the tissue signal (which has higher singular values) and the noise (which has lower singular values). Selecting one or more appropriate singular value cutoffs for SVD filtering is, therefore, important for extracting blood signal from tissue and noise.

Traditional SVD filtering methods assume globally homogeneous tissue characteristics and uniform noise distribution, and therefore perform SVD processing on an entire data set. However, the performance of SVD clutter filtering is significantly compromised when imaging tissues with different characteristics, or when imaging tissues with a large range of depth where ultrasound noise distribution is not uniform. In addition, a robust adaptive cutoff selection scheme has not been proposed to isolate blood signal from both tissue and noise.

The systems and methods described here overcome these limitations by implementing a local low-rank matrix decomposition ("LRMD") analysis that can adaptively select cutoff values for blood signal extraction by taking advantage of locally homogenous tissue characteristics and approximately uniform noise distribution when using a local processing window.

Referring now to FIG. 1, a flowchart is illustrated as setting forth the steps of an example method for generating an image that depicts blood flow in a subject's vasculature, which may include small vessels, based on ultrasound signal data. The method includes providing data acquired with an ultrasound imaging system, as indicated at step 102. The provided data can generally include an input data matrix. In some embodiments, the input data matrix is a three-dimensional matrix having two dimensions associated with spatial direction and one dimension associated with time. In some other embodiments, the input data matrix is a four-dimensional matrix having three dimensions associated with spatial directions and one dimension associated with time. As one example, the input data matrix can be an $N_x \times N_z \times N_t$ matrix.

The provided data are then divided into submatrices, as indicated at step 104. As one example, when the input data matrix is an $N_x \times N_z \times N_t$ matrix, each submatrix can be an $n_x \times n_z \times n_t$ matrix where $n_x \leq N_x$, $n_z \leq N_z$, $n_t \leq N_t$, and $n_x \cdot n_z \geq n_t$. In some embodiments, the submatrices are spatially distinct; however, in some other embodiments, some or all of the submatrices can be spatially overlapped with each other. In general, the size of each submatrix should be chosen so local tissues within each submatrix window have similar characteristics, such as temporal coherence, speckle, and noise characteristics. In some embodiments, the data submatrices can all have the same size; however, in other embodiments, some or all of the data submatrices can be differently sized. The amount of overlap between submatrix windows should be chosen so smooth angiography maps can be generated.

Each submatrix is then processed to extract signals associated with blood vessels. In this process, each data submatrix is first decomposed by means of a low-rank matrix decomposition or factorization technique, as indicated at step 106. The low-rank matrix decomposition or factorization can be implemented with at least one of the Karhunen-Loève transform ("KLT"), singular value decomposition ("SVD"), eigenvalue decomposition ("EVD"), principal component analysis ("PCA"), and so on. In general, this process will generate decomposed matrix values based on the input data submatrices.

As one example, performing EVD will generate decomposed matrix values as eigenvalues. As another example, performing an SVD will generate decomposed matrix values as singular values. Decomposing a data submatrix using an SVD technique also results in (unitary) singular vector matrices, U and V. The singular values are sorted in descending order, with lower-order singular values being greater than higher-order singular values. The right singular vectors, V, are sorted following the same order of the singular values. Tissue signal typically resides in the lower-order singular values and noise signal typically resides in the high-order singular values.

The decomposed matrix values generated during the LRMD can be used to extract the vessel signals from the data submatrices. The decomposed submatrices are then processed to determine one or both of a low-order cutoff value and a high-order cutoff value, as indicated at process block 108. The specific order in which the low-order and high-order cutoff values can be determined can be swapped (i.e., the high-order cutoff can be determined first or second, or in some instances in parallel). As one example, when the low-rank matrix decomposition implements SVD, the singular values and vectors are processed to determine a low-order singular value cutoff and a high-order singular value cutoff. In other implementations, the low-order and high-order cutoff values are based on other decomposed matrix values, such as eigenvalues. Example methods for determining low-order and high-order cutoff values are now described with respect to FIGS. 2A-2B and 3A-3B.

Figure 2A:
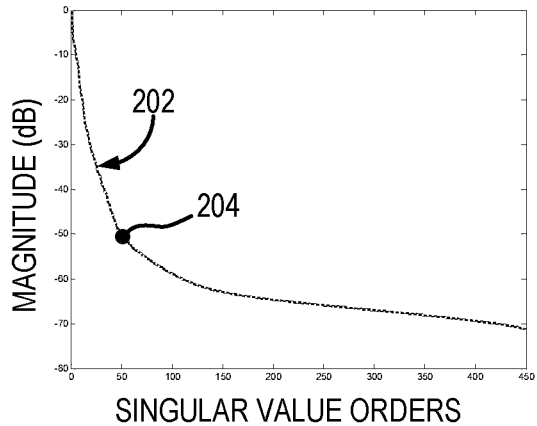
FIG. 2A is an example plot of singular values computed from an ultrasound data submatrix, and illustrates an example of estimating a low-order singular value cutoff.
Figure 2B:
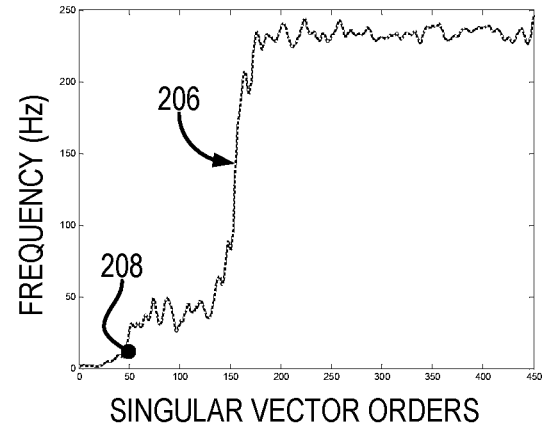
FIG. 2B is an example plot of singular vector frequencies computed from an ultrasound data submatrix, and illustrates an example of estimating a low-order singular value cutoff.

FIGS. 2A and 2B illustrate two different example methods for determining a low-order singular value cutoff. These two methods can be used separately or combined to co-determine the low-order singular value cutoff value.

FIG. 2A shows a singular value curve 202 that can be used to evaluate the decay rate of the singular values in a decomposed data submatrix in order to identify a low-order singular value cutoff that differentiates tissue signal from vessel flow signal. The decay rate can be calculated by at least one of gradient calculation methods, fitting methods, and so on. A threshold value for the decay rate can be predetermined to identify the low-order singular value cutoff point 204. As will be described below, all singular values with order below the low-order singular value cutoff can then be set to zero, or weighted using a small weighting factor, to suppress tissue signals.

FIG. 2B shows a singular vector frequency curve 206, which is obtained by estimating the mean frequency of each of the singular vectors. The mean frequency of a singular value vector can be calculated by lag-one autocorrelation, spectrum weighting, or any other suitable method. Tissue signal typically presents at low oscillating frequencies, and noise signal typically presents at high oscillating frequencies. Therefore, using a pre-determined low-frequency cutoff value, a low-order singular value cutoff point 208 can be determined from the singular vector frequency curve 206. As mentioned above and described below, all singular values with order below the low-order singular value cutoff can then be set to zero, or weighted using a small weighting factor, to suppress tissue signals.

Figure 3A:
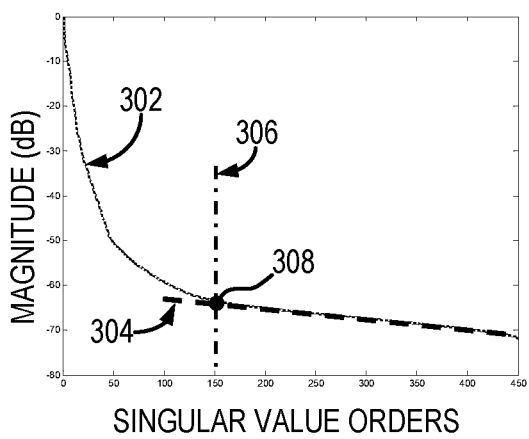
FIG. 3A is an example plot of singular values computed from an ultrasound data submatrix, and illustrates an example of estimating a high-order singular value cutoff.
Figure 3B:
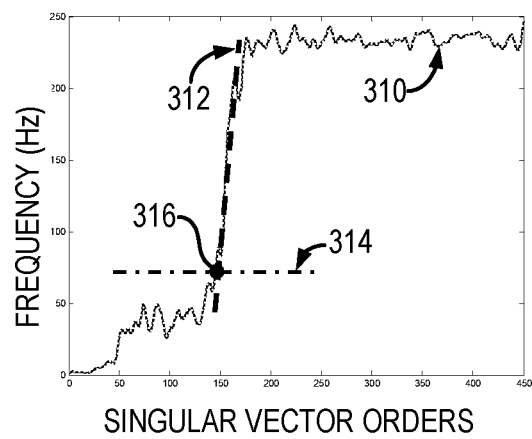
FIG. 3B is an example plot of singular vector frequencies computed from an ultrasound data submatrix, and illustrates an example of estimating a high-order singular value cutoff.

FIGS. 3A and 3B illustrate two different example methods for determining a high-order singular value cutoff. These two methods can be used separately or combined to co-determine the low-order singular value cutoff value.

FIG. 3A shows a singular value curve 302, which can be used to determine the high-order singular value cutoff point 308. The Marčhenko-Pastur law states that the spectral distribution of an independent and identically distributed ("i.i.d.") complex Gaussian random matrix is approximately linear with slope dependent on the dimensions of the matrix. In post-beamforming ultrasound images, (non-speckle) noise is uniformly distributed and can be approximated as Gaussian in the near field. In the far field, noise is generally assumed to be locally uniform and approximated as a local Gaussian distribution. Therefore, at least some component of the singular value distribution of a matrix constructed from 2D or 3D ultrasound data should be quasi-linear. A fitted line 304 can be obtained by linear fitting the higher-order singular values, which represent noise signals. The point from which the singular value curve 302 begins to deviate from the fitted line 304 at line 306 can be used as the high-order singular value cutoff point 308. A predetermined threshold of the amount of deviation can be used to identify the high-order singular value cutoff point 308. As will be described below, all singular values with order above the high-order singular value cutoff can then be set to zero, or weighted using a small weighting factor, to suppress noise signals.

FIG. 3B shows a singular vector frequency curve 310. A sharp transition area will generally be present between the flow signal and the noise signal, and the shape of this transition area is quasi-linear. To this end, a fitted line 312 can be obtained by linear fitting of the transition area. The point from which the singular vector frequency curve 310 begins to deviate from the fitted line 312 from the low singular vector-order side of the curve at line 314 can be used as the high-order singular value cutoff point 316. As mentioned above and described below, all singular values with order above the high-order singular value cutoff can then be set to zero, or weighted using a small weighting factor, to suppress noise signals.

As another example, the low-order cutoff value and high-order cutoff value can be determined using a statistical estimation method, such as Stein's Unbiased Risk Estimator ("SURE").

Referring again to FIG. 1, the low-order and high-order cutoff values can be analyzed to assess their fidelity and likelihood to produce an image with the desired signal components from the subject's vasculature, which may include small vessels, as determined at decision block 110 and indicated at step 112. For example, a set of rules can be made and implemented to determine the robustness of the selected low-order and high-order cutoff values. Based on the analysis performed in step 112, a determination is first made whether the data submatrix should be processed to extract blood flow signals, as indicated at decision block 114. If not, then the data submatrix is removed from the processing pipeline. For instance, the analysis performed in step 112 will indicate that there is no blood flow signal to be extracted from the data submatrix. In these instances, the submatrix block can be skipped by forcing all entries in the data to zero or null values.

If the data submatrix is to be processed, however, then as indicated at decision block 116, a determination is then made whether the cutoff values should be kept or rejected based on the analysis performed in step 112. As one example, if the analysis of the cutoff values at step 112 determines that using the cutoff values would likely result in vessel signals not being extracted from the input data, then the cutoff values can be rejected as indicated at decision block 116 and new cutoff values can be determined by performing step 108.

As one example, one rule in the set of rules implemented in the analysis at step 112 can include determining if the high-order cutoff value is smaller than or equal to the low-order cutoff (i.e., if the low-order cutoff value is greater than the high-order cutoff value). As another example, a rule in the set of rules implemented in the analysis at step 112 can include determining if the difference between the high-order and low-order cutoff values is smaller than a threshold value. As still another example, a rule in the set of rules implemented in the analysis at step 112 can include determining whether the difference between the high-order and low-order cutoff values is greater than a particular threshold value. If any of these foregoing rules are satisfied, then the data submatrix can be skipped as determined at decision block 114 or the cutoff values rejected as determined at decision block 116.

If no fidelity check is performed, or if the fidelity check confirms that the data submatrix should be processed using the determined cutoff values, then the cutoff values are used to extract the blood flow signal from the data submatrix, as indicated at step 118. In general, the data submatrix is processed using the low-order and high-order cutoff values such that decomposed matrix values in the decomposed data submatrix that have an order that is lower than the low-order cutoff and higher than the high-order cutoff are suppressed or otherwise weighted by zero-values or low-valued weighting coefficients. For instance, when the data submatrices are decomposed using SVD, the singular values with orders lower than the low-order singular value cutoff and higher than the high-order singular value cutoff can be suppressed by forcing them to zero, or can be weighted using small coefficients. The processed singular values are then used to reconstruct the vessel flow signal by reversing the SVD calculation.

A determination is then made at decision block 120 whether all of the desired data submatrices have been processed. If not, then the next data submatrix is selected for processing, as indicated at step 122. Otherwise, the extracted blood flow signals are then combined to form an angiography image, as indicated at step 124. The generated image can then be displayed or stored as desired, as indicated at step 126.

Figure 4:
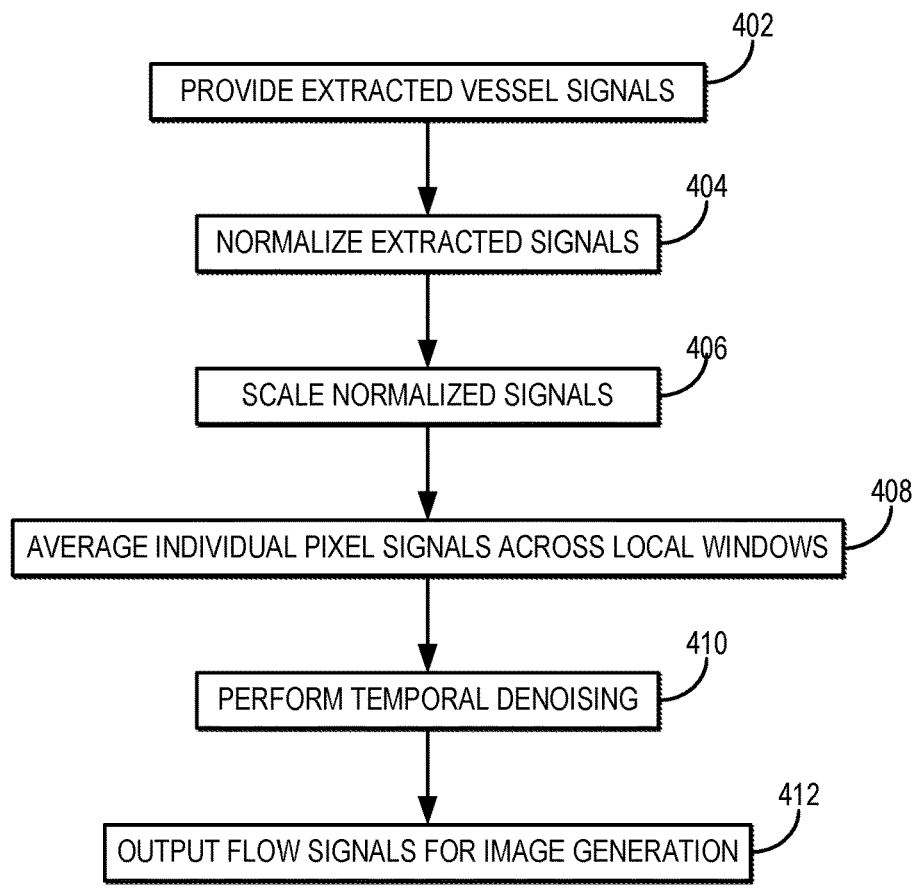
FIG. 4 is a flowchart setting forth the steps of an example method for combining vessel image signals extracted from ultrasound data submatrices.

An example method for combining the extracted vessel signals is illustrated in FIG. 4, which shows a flowchart setting forth the steps of an example method for combining such extracted signals. In this example method, the extracted vessel signal data are provided to a processor or computer system for combination, as indicated at step 402. The submatrix vessel data are first normalized, as indicated at step 404. For instance, the vessel signals can be normalized by the sum of the processed singular values used in flow signal reconstruction in step 118 above. The normalization process provides uniform intensity of the blood flow signal map throughout the field-of-view. The normalized data can then be scaled, as indicated at step 406. As one example, the normalized data are scaled by the ratio of non-zero input data to eliminate artificial enhancement of the signal intensity when the submatrix includes areas with zero pixel values outside the ultrasound field-of-view.

For each spatial pixel, the final flow signal is obtained by averaging the signal values at that pixel location across each local window submatrix that includes that particular spatial pixel, as indicated at step 408. As an example, for a set of local windows, $W=\{W_1, W_2, W_3, W_4, W_5\}$, containing five local windows, if a given pixel location, p, is contained in three of the local windows, (e.g., $W_1$, $W_2$, and $W_3$), then the final flow signal at that pixel location, p, would be the average of the signals at the pixel location, p, in those three local windows, $W_1$, $W_2$, and $W_3$, that contain the pixel location.

Flow signals can be further denoised by temporal denoising filters, as indicated at step 410. As one example, the temporal denoising filter can be based on the temporal behavior of the signal at a pixel location, and can be implemented using at low-pass filters, high-pass filters, band-pass filters, or combinations thereof. For noise, the spectrum is supposed to be evenly distributed energy across the frequency range (i.e., the noise should be white noise). However, residual energy in the low frequency spectrum can be mistakenly counted as blood signal. A temporal high-pass filter with a predefined low cutoff frequency can be used to remove such low-frequency component. This filtering can be performed for each individual pixel throughout the image.

In addition, the characteristics of spectrum of the time signal at a pixel location can be used to further differentiate blood signal from noise. For noise, the positive and negative spectra tend to be symmetric, but for blood signal, the positive and negative spectra tend to be asymmetric. Therefore, noise can be identified based on evaluating the symmetry of the positive and negative spectra, which can be determined based on a sum of the absolute difference, a cross-correlation, shape similarity measurements, or any other suitable methods. Once the noise pixels are identified based on temporal spectral characteristics, masks can be created to reject or suppress noise pixels.

After the signals have been denoised, the final vessel flow signal can be output for image generation, as indicated at step 412. As one example, the vessel flow signal data can be processed using well-established blood flow processing methods, including color flow imaging, spectral Doppler, power Doppler, vector flow imaging, blood flow imaging, and so on.

Figure 5:
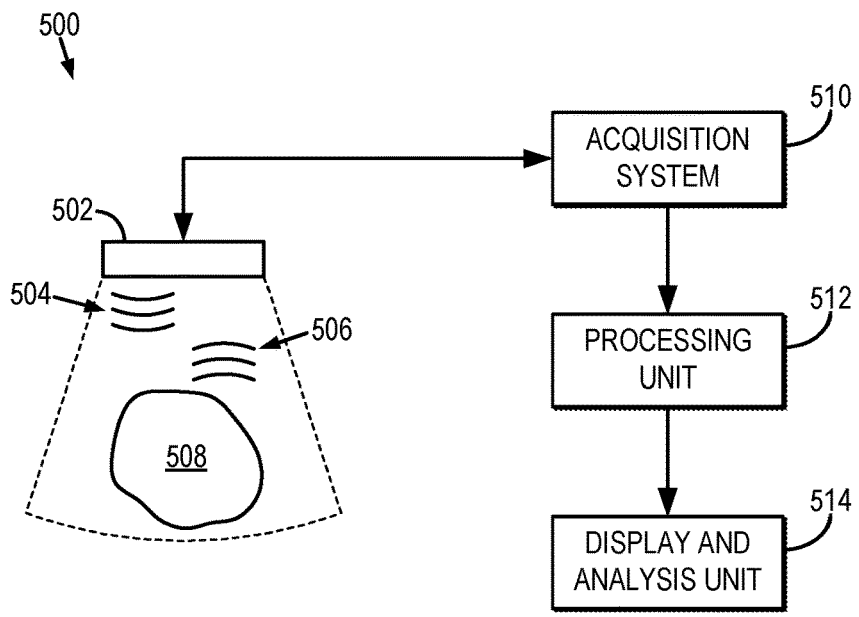
FIG. 5 is a block diagram of an example ultrasound imaging system that can implement the methods described here.

FIG. 5 illustrates the main components of an example ultrasound imaging system 500 that can implement the methods described here. The system 500 generally includes an ultrasound transducer 502 that transmits ultrasonic waves 504 and receives ultrasonic echoes 506 from an object 508, which may be tissue in a subject. An acquisition system 510 acquires ultrasound signals from the transducer 502 and outputs the signals to a processing unit 512, which can include a suitable computer system or processor. In some implementations, the acquisition system 510 beamforms the signal from each transducer element channel and outputs the signal to the processing unit 512. The processing unit 512 can be programmed to implement the methods described here for generating images that depict or quantify blood flow in a subject's vasculature, including in small vessels. The output from the processing unit 512 can be displayed and analyzed by a display and analysis unit 514, which can include a suitable computer display or computer system.

The acquisition system 510 can have a high imaging frame and volume rate, such that the acquisition pulse-repetition-frequency ("PRF") can be at least 100 Hz. The system 500 can sample and store at least one hundred ensembles of ultrasound signals in the temporal direction.

The ultrasound system 500 can transmit and receive at least one of focused waves, diverged waves, spherical waves, cylindrical waves, and plane waves. The ultrasound system 500 can implement a detection sequence that includes one of conventional line-by-line scanning, compounding plane wave imaging, and compounding diverging beam imaging. Furthermore, the transmit pulses generated by the ultrasound system 500 can include at least one of conventional non-coded imaging pulses and spatially or temporally encoded pulses. The receive pulses generated by the ultrasound system 500 can in some instances be generated based on at least one of fundamental frequency and harmonic frequencies.

The processing unit 512 can compute or otherwise obtain ultrasound blood flow signals using the methods described here, and in some instances using clutter filtering that rejects the tissue signal. The processing unit 512 can also implement noise equalization techniques, such as those described below, to equalize blood flow signals. In some embodiments, the noise-equalized blood flow signals can be processed by the processing unit 512 to obtain desired hemodynamic measurements of the blood, display the results, and so on.

The use of unfocused or weakly-focused ultrasound waves such as plane waves and wide beams is useful for high frame-rate ultrasound blood flow imaging. Unfocused or weakly-focused waves can cover a much larger field-of-view ("FOV") per pulse-echo cycle than focused waves, and therefore these waves can provide much more information for robust tissue clutter rejection and blood flow signal extraction. However, due to the lack of transmit focusing, the signal-to-noise-ratio ("SNR") of unfocused and weakly-focused waves deteriorates much more quickly than focused waves along the depth direction.

The noise level compared to echo signal at deeper depth of the tissue is typically much higher than that at shallower depth of tissue, causing a non-uniform noise distribution that hampers blood flow imaging quality. This drop of SNR and increase in noise with depth cannot be readily compensated by the conventional time-gain-compensation ("TGC") control of the ultrasound system, and can greatly undermine the blood flow imaging quality of high frame-rate unfocused and weakly-focused waves. This uneven noise distribution should therefore be equalized or otherwise compensated to facilitate robust high frame-rate blood flow imaging.

Figure 6:
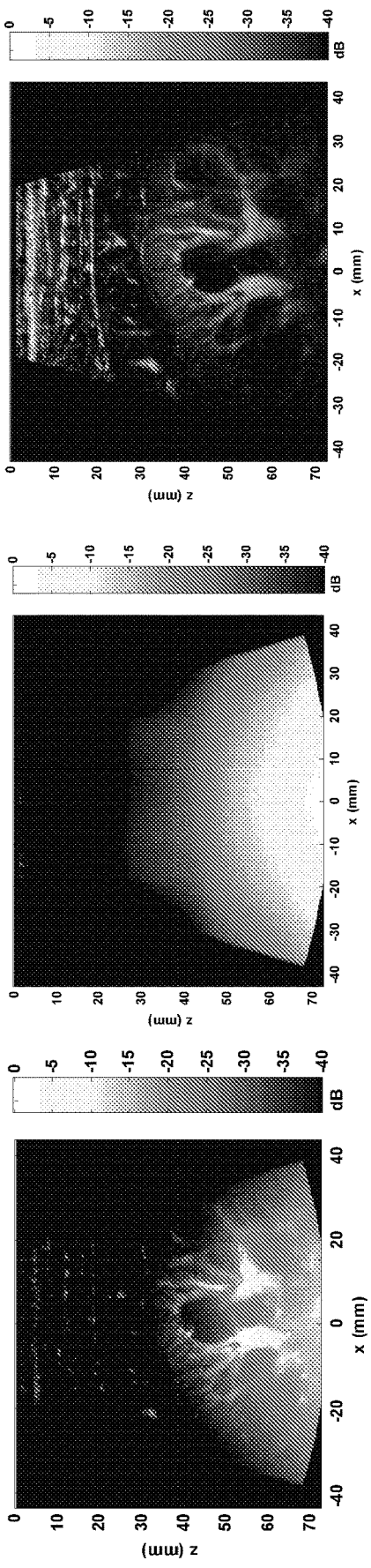
FIG. 6A is an example small blood vessel image generated using a global adaptive cutoff technique and depicting severe background noise contamination.
FIG. 6B is an example noise profile estimated from a tissue-mimicking phantom.
FIG. 6C is an example small blood vessel image generated by removing the background noise in FIG. 6A using the noise profile in FIG. 6B.

As described above, as an alternative to performing the blood flow signal processing method described above on submatrix data, the method can be performed on the entire input data. That is, the adaptive cutoff selection methods described above can be applied to the input data matrix, rather than the individual data submatrices, to extract the blood flow signal. An example image generated using this global processing, rather than the local processing based on data submatrices, is shown in FIG. 6A. It can be seen that the image produced in this manner is severely contaminated by background noise. The significant noise levels in this image are present because when processing the whole data set, the spatial distribution of noise is not uniform, which violates the low-rank matrix decomposition assumptions.

Described here now are techniques for effectively and efficiently equalizing, or otherwise compensating, the noise of blood flow images acquired by high frame-rate ultrasound. In general, the methods described below use an estimated noise field to equalize the blood flow signal (or image) to achieve better visualization of the vessel perfusion. However, the noise field generated by the different methods can also be used to create a spatially weighted data fidelity term for use within a model-based image reconstruction or decomposition, such as low-rank plus sparse decomposition. Because ultrasound noise is not spatially independent and identically distributed (i.i.d.), the performance of reconstruction and decompositions such as low-rank plus sparse is generally compromised. The integration of a fidelity term derived from the noise field obtained with the methods introduced here, however, can facilitate a more robust low-rank plus sparse decomposition for applications such as clutter filtering.

In one example, to address the problems associated with a non-uniform distribution of noise, the background noise can be reduced, removed, or otherwise visually diminished by acquiring a set of reference signals from a tissue-mimicking phantom and obtaining the noise profile from these reference signals. An example noise profile acquired in this manner is shown in FIG. 6B. The original image can then be processed to compensate for the noise in the image using this noise profile, the result of which is shown in FIG. 6C. As one example, effects from unequal distribution of the noise in the original image can be reduced by dividing the original image by the noise profile. In this particular example, the effect of the unequal noise distribution is reduced by effectively boosting the signal and noise in the upper region of the image in FIG. 6A while effectively suppressing the signal and noise in the lower region of the image in FIG. 6A. This processing balances the signal and noise within a given dynamic range, thereby diminishing the visual depiction of noise in the processed image shown in FIG. 6C. The noise profile can also be estimated analytically based on the ultrasound system configurations and the tissue characteristics, as will be described below.

Figure 7:
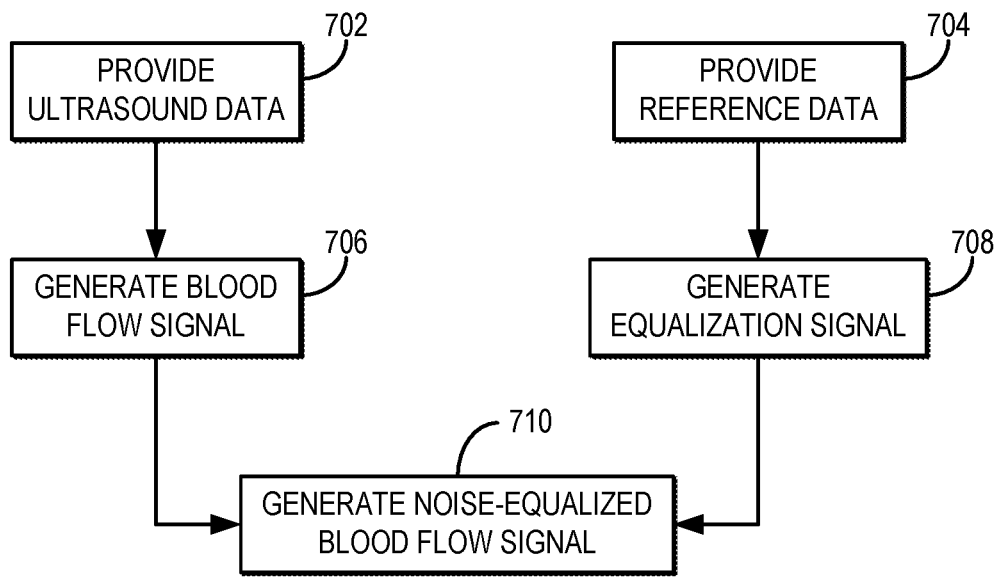
FIG. 7 is a flowchart setting forth the steps of an example method for equalizing a non-uniform noise distribution in a blood flow signal generated from ultrasound data, wherein the noise equalization is implemented based on reference data.

Referring now to FIG. 7, a flowchart is illustrated as setting forth the steps of an example method for equalizing a non-uniform noise distribution in a blood flow signal generated from ultrasound data, wherein the noise equalization is implemented based on reference data. In this method, ultrasound data are provided to a computer system, as indicated at step 702, and reference data are also provided to the computer system, as indicated at step 704. These data can be provided by acquiring the data with an ultrasound imaging system, or by retrieving previously acquired data from data storage. This latter approach can be especially useful for providing previously acquired reference data based on the imaging sequence parameters, system configuration parameters, or both, used when acquiring the ultrasound data.

In general, the two sets of data are acquired using the same ultrasound imaging sequence (e.g., same transmit pulse, same receive filters) and system configurations (e.g., same gain settings, same transmit voltages, same ultrasound transducers). The ultrasound data are acquired from the tissue in which blood flow is being examined, and the reference data are acquired from a reference phantom that has similar acoustic properties (e.g., similar speed of sound, similar acoustic attenuation) as the targeted tissue. If the imaging sequence, the system configurations, and the acoustic properties of the targeted tissue remain unchanged or vary only slightly, the reference phantom data may only need to be acquired once. Thus, in some embodiments, it can be possible to retrieve and use previously acquired reference data associated with similar imaging sequence, system configurations, and acoustic properties of the targeted tissue from data storage.

The two sets of data are then processed such that a blood flow signal (or a blood flow image) is generated from the ultrasound data, as indicated at step 706, and such that an equalization signal (or an equalization image) is generated from the reference data, as indicated at step 708. In both instances, the signals can be generated using the techniques described above. As described above, the blood flow signal is not noise-equalized. Because the reference phantom data does not have blood flow signal (i.e., a pure tissue signal), the majority of the remaining signal after blood flow processing is noise, which can be used to serve as the equalization signal to equalize noise of the targeted blood flow signal.

From the blood flow signal and the equalization signal, a noise-equalized blood flow signal (or noise-equalized blood flow image) is generated, as indicated at step 710. As one example, the noise-equalized blood flow signal can be generated by dividing the blood flow signal by the equalization signal, as mentioned above. As another example, the noise-equalized signal can be generated by computing a difference between the blood flow signal and the equalization signal. In some embodiments, the equalization signal can be processed by a smoothing filter prior to equalization to provide more robust division or subtraction.

The reference phantom that is scanned to provide the reference data can be built to mimic specific tissue acoustic properties at specific locations. For example, for abdominal imaging, the phantom may have higher acoustic attenuation and lower speed of sound in the near field to mimic subcutaneous fat tissue, and lower acoustic attenuation and regular speed of sound in the mid-range and far field to mimic soft tissues such as liver. The reference phantom data can be acquired with all possible combinations of ultrasound imaging sequences, system configurations, tissue acoustic properties, and so on, to construct a look-up database from which relevant reference data can be retrieved and provided to the computer system. The system or the user can select the equalization signal from this look-up database without the necessity of acquiring new reference phantom data. This is particularly important for real-time blood flow imaging.

In another example, non-uniform noise in the blood flow signal can be equalized using high-order singular vector techniques. When performing a singular value decomposition ("SVD") on ultrasound data that has both spatial and temporal information, tissue signal is generally represented by the low-order, large singular values, blood signal is generally represented by mid-range singular values, and noise is generally represented by the high-order, small singular values. This distribution of singular values stems from the ultrasound backscattering signal strength and the temporal behavior of the different components of the signal (e.g., tissue has high backscattering signal, but moves slowly in time, while blood has weak backscattering signal, but moves fast in time).

Figure 8:
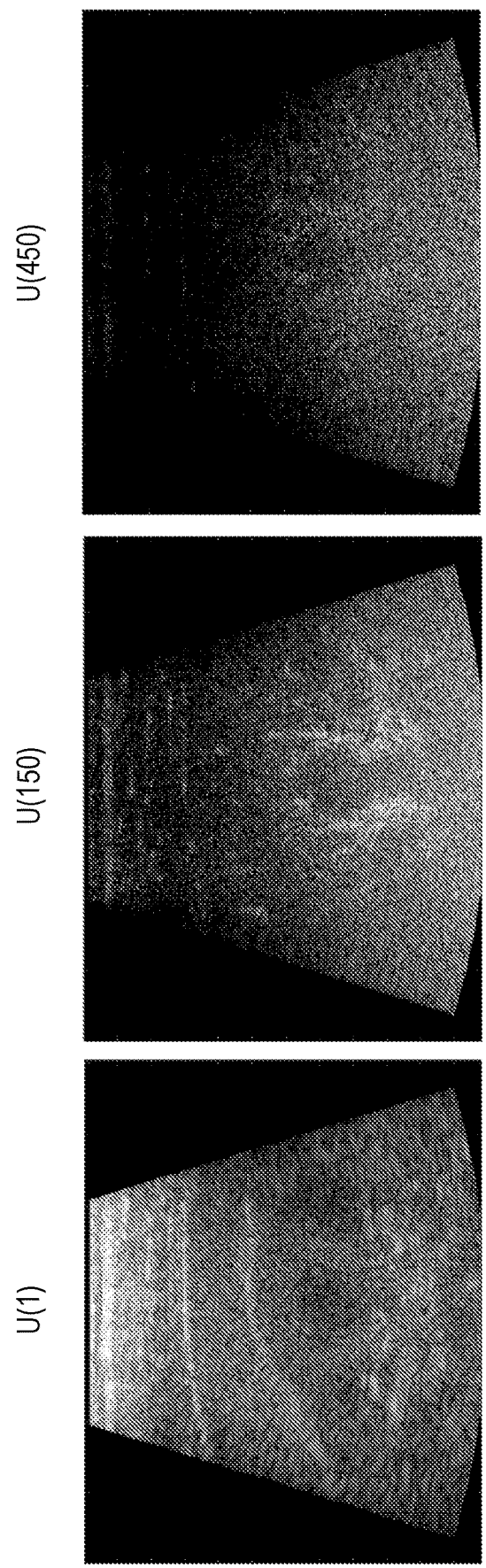
FIG. 8 illustrates low-order, mid-order, and high-order singular value maps derived from ultrasound data.

After the SVD calculation, the ultrasound signal is decomposed into a unitary matrix, U (i.e., left singular vectors), that provides the spatial information; a rectangular diagonal matrix, D, whose diagonal entries are singular values; and another unitary matrix, V (i.e., right singular vectors), that provides the temporal information. The unitary matrix U can be used to derive a noise field that can be used to equalize the blood flow signal. As shown in FIG. 8, for a rank-450 ultrasound kidney blood flow signal, the low-order singular vector U(1) mostly represents tissue, the mid-order singular vector U(150) mostly represents blood, and the high-order singular vector U(450) mostly represents noise.

Figure 9:
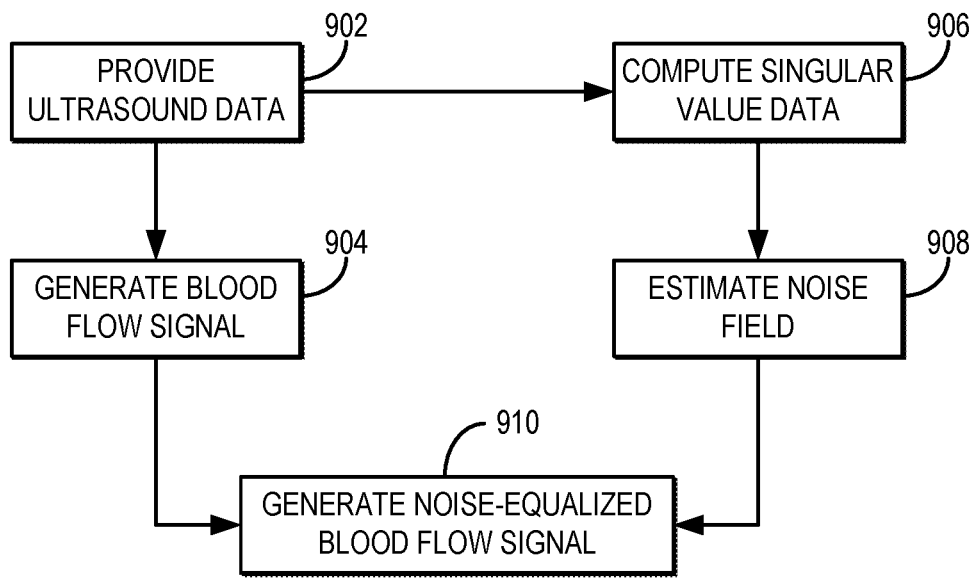
FIG. 9 is a flowchart setting forth the steps of an example method for equalizing a non-uniform noise distribution in a blood flow signal generated from ultrasound data, wherein the noise equalization is implemented using a high-order singular-vector-based technique.

Referring now to FIG. 9, a flowchart is illustrated as setting forth the steps of an example method for equalizing a non-uniform noise distribution in a blood flow signal generated from ultrasound data, wherein the noise equalization is implemented using a high-order singular-vector-based technique. The method includes providing ultrasound data to a computer system, as indicated at step 902. The data can be provided by acquiring the data with an ultrasound imaging system, or by retrieving previously acquired data from data storage. The ultrasound data are then processed to generate a blood flow signal (or blood flow image), as indicated at step 904. For instance, the blood flow signal can be generated using the methods described above.

The ultrasound data are also processed to generate singular value data, as indicated at step 906. The singular value data generally includes high-order singular values, mid-order singular values, and low-order singular values. The singular value data may also include separated spatial information and separated temporal information, such as may be embodied in left unitary and right unitary matrices, respectively. As one example, the singular value data are generated by computing a singular value decomposition of the ultrasound data. As other examples, however, the SVD operation can implement randomized singular value decomposition (rSVD), a Karhunen-Loève transform ("KLT"), eigenvalue decomposition ("EVD"), power iteration, principal component analysis ("PCA"), or so on.

A noise field can be estimated from the singular value data, as indicated at step 908. For robust noise equalization, the high-order singular vectors can be smoothed by means of spatial smoothing filters (e.g., a two-dimensional median filter), or the average or median value of the high-order singular values of all the pixels at each depth can be used to derive a depth-dependent noise curve, which can then be smoothed and replicated along the lateral dimension to obtain a noise field. Other methods can also be used to come up with a reliable noise field from one or more high-order singular values. As mentioned, the noise field can be estimated based on one high-order singular value, or based on multiple high-order singular values. For example, U(440) through U(450) can be averaged to smooth the noise field. The high-order singular value cutoff selection method described above can be used to determine the range of singular vectors that can be used for noise field estimation.

Figure 10:
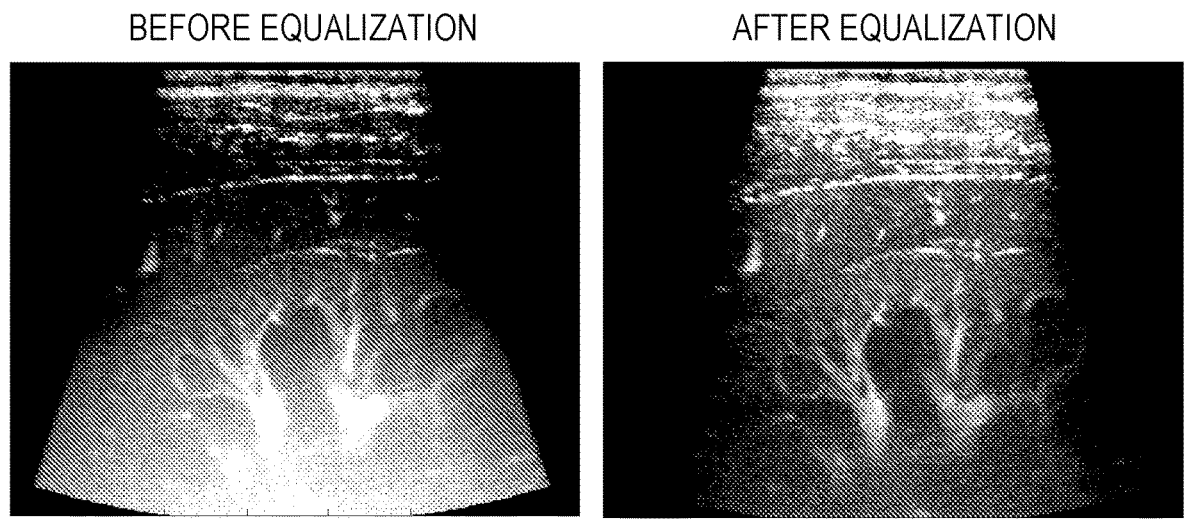
FIG. 10 illustrates an example of a blood flow image before and after noise equalization using a singular vector-based technique.

After the noise field is estimated, it can be used to generate a noise-equalized blood flow signal (or noise-equalized blood flow image), as indicated at step 910. As one example, the noise-equalized blood flow signal can be generated by dividing the blood flow signal by the noise field. As another example, the noise-equalized signal can be generated by computing a difference between the blood flow signal and the noise field. In some embodiments, the noise field can be processed by a smoothing filter prior to equalization to provide more robust division or subtraction. An example blood flow image before and after noise equalization using these techniques is illustrated in FIG. 10.

It is noted that the high-order singular vector-based equalization introduced here can be applied to any clutter filters for noise equalization, and not only SVD-based clutter filters. For SVD-based clutter filters, this method is particularly convenient because SVD has already been calculated for clutter filtering, and therefore no additional SVD needs to be calculated for the purpose of noise equalization.

Figure 11:
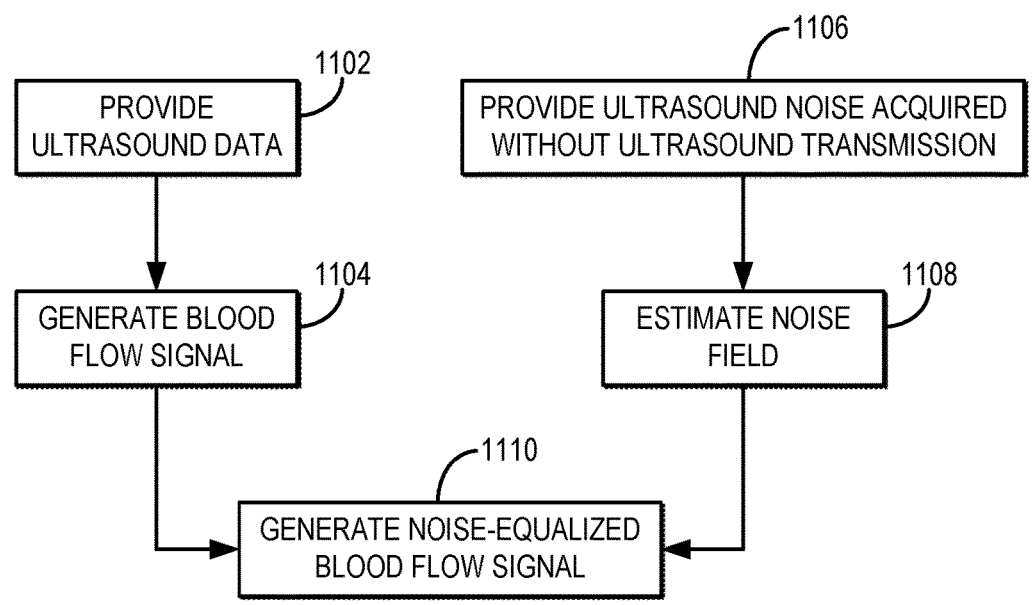
FIG. 11 is a flowchart setting forth the steps of an example method for equalizing a non-uniform noise distribution in a blood flow signal generated from ultrasound data, wherein the noise equalization is implemented based on experimentally measured noise data.

In another example, the noise can be directly measured from the ultrasound system, and can then be used to equalize the noise of the blood flow signal. Referring now to FIG. 11, a flowchart is illustrated as setting forth the steps of an example method for equalizing a non-uniform noise distribution in a blood flow signal generated from ultrasound data, wherein the noise equalization is implemented based on experimentally measured noise data. The method includes providing ultrasound data to a computer system, as indicated at step 1102. The data can be provided by acquiring the data with an ultrasound imaging system, or by retrieving previously acquired data from data storage. The ultrasound data are then processed to generate a blood flow signal (or blood flow image), as indicated at step 1104. For instance, the blood flow signal can be generated using the methods described above.

Ultrasound noise data are also provided to the computer system, as indicated at step 1106. The ultrasound noise data can be provided by acquiring the data with an ultrasound imaging system, or by retrieving previously acquired data from data storage. The noise is obtained by turning off the ultrasound transmission (e.g., setting acoustic output to zero), and receiving data with the same imaging sequence (e.g., same transmit pulse, same receive filters) and system configuration (e.g., same gain settings, same transmit voltages, same ultrasound transducers) as those used for blood flow signal acquisition. Because no ultrasound pulse is being transmitted, the received signals will be all zeros except for the system noise.

A noise field, (or equalization signal) can be estimated from this ultrasound noise data, as indicated at step 1108. After the noise field is estimated, it can be used to generate a noise-equalized blood flow signal (or noise-equalized blood flow image), as indicated at step 1110. As one example, the noise-equalized blood flow signal can be generated by dividing the blood flow signal by the noise field. As another example, the noise-equalized signal can be generated by computing a difference between the blood flow signal and the noise field. In some embodiments, the noise field can be processed by a smoothing filter prior to equalization to provide more robust division or subtraction.

The ultrasound noise data can be smoothed and processed similarly to the methods described above for noise equalization. Multiple noise fields can also be estimated to obtain an averaged noise field for more robust noise equalization. When the imaging sequence or the system configuration changes, a new noise field should be measured for equalization, unless the change is subtle and the noise field is not being altered significantly. Similar to the reference phantom approach, a look-up database of the noise field for all possible combinations of imaging sequences and system configurations can be established, facilitating real-time implementation of this technique.

The noise field can be measured on a tissue mimicking phantom, in water, in air, or on the targeted tissue with transmission power turned off. When collecting the noise from phantoms or water or air, this method does not account for the noise from the targeted tissue (e.g., noise from tissue attenuation, phase aberration) and assumes that the noise is purely from the ultrasound system. However, when collecting the noise from the targeted tissue, this method does partially account for the noise from the targeted tissue.

It is noted that it may not be practical to establish a look-up database for the noise collected from tissue because of the potential differences in tissue between subjects. In these instances, the targeted tissue first can be located, the transmission power turned off to collect a noise field for the targeted tissue as described above, and then the following images can be equalized with the noise field. For imaging similar tissues or adjacent tissues close to the targeted tissue, and small alterations of the imaging sequences and system configurations, the noise field may not need to be recollected.

In those instances where the transmission power is turned off, the transmission power can be considered as "turned off" by reducing the voltage of the ultrasound transmitter to as close to 0 V as possible, reducing the duty cycle of the ultrasound transmit pulse to as close to zero percent as possible, reducing the transmit aperture size to as close to 0 mm as possible, or combinations of these settings.

In another example, a noise propagation-based equalization method that is based on experimentally measured ultrasound noise data can be used to equalize the non-uniform noise in a blood flow signal. This noise propagation-based method only needs a single measurement of the system noise from each transducer element, and can then derive a theoretical noise field based on the given imaging sequence and system configuration.

Figure 12A:
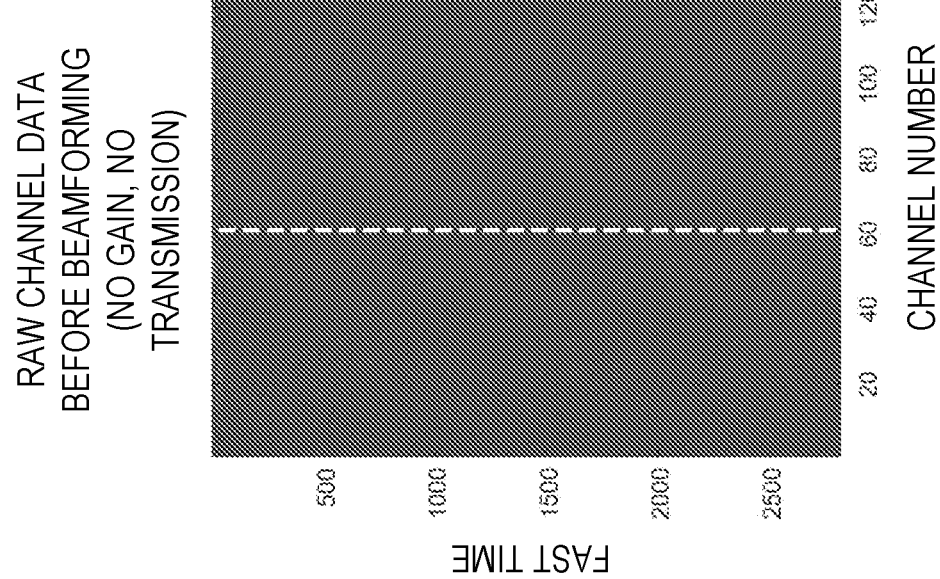
FIG. 12A depicts noise from ultrasound channels with no gain or transmission, illustrating no depth-dependence to the noise.
Figure 12B:
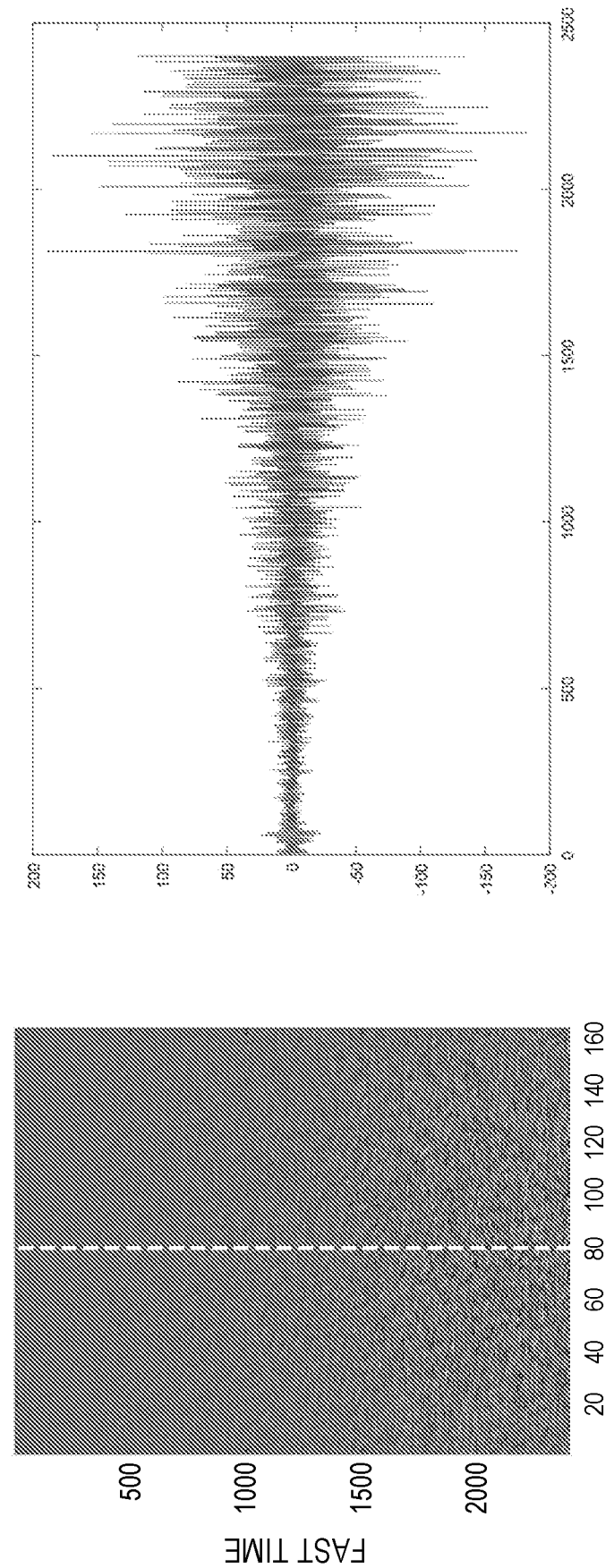
FIG. 12B depicts noise from ultrasound channels with a typical gain setting and with beamforming, illustrating a depth-dependence to the noise.

As shown in FIGS. 12A and 12B, with the transmission power turned off and zero gain from the ultrasound system, the noise from the ultrasound element channels (FIG. 12A) is depth independent and approximately follows a Gaussian distribution. The plot on the right-hand side of FIG. 12A shows a single channel data set from the data shown on the left-hand side, from it can be seen that the variance of the signal does not change along depth. This is contrary to the depth-dependent noise field because no gain setting or beamforming has been applied. However, after applying a typical gain setting and performing the beamforming process, the noise becomes depth-dependent (i.e., the deeper the tissue, the higher the noise), as shown in FIG. 12B.

The reason for the evolvement of depth-independent Gaussian noise to the depth-dependent non-Gaussian noise is two-fold. First, the noise-gain characteristic of the ultrasound system amplifiers (e.g., TGC gain and other amplifiers in the frontend of the system) is nonlinear. That is, the amplifiers have much higher noise at higher gains than at lower gains. In deep tissue regions where the gain setting is typically high, the resulting noise from the system amplifiers is also significantly higher. The second factor is the beamforming process. For software-based beamforming or beamforming with dynamic receive aperture (i.e., fixed F-number), the ultrasound signal at each beamformed pixel is a weighted sum (i.e., receive apodization) of a collection of ultrasound elements whose emissions contributed to the backscattered signal from this pixel.

Depending on the spatial location of the pixel, the number of elements used for beamforming can be significantly different. For example, a pixel that is close to the surface of the transducer may only need 10 elements for beamforming, but a pixel that is far away from the surface of the transducer may need all the available elements (e.g., 128) of the transducer for beamforming. The different number of beamforming elements can cause different amount of noise accumulation for each spatial pixel, which in turn causes the depth-dependent and location-dependent noise behavior.

Based on the noise-gain characteristics of an ultrasound system, which can be either experimentally measured or obtained from the manufacturer, and the beamforming process used to construct the raw channel data into final ultrasound signals, the final noise field can be derived using noise propagation. To experimentally determine the noise-gain characteristics of the ultrasound system, one set of data with no gain and one set of data with known gain settings can be acquired and used to calculate the ratio of the noise amplitude. Then, the noise amplification at each gain setting can be derived by methods, such as curve fitting.

Figure 13:
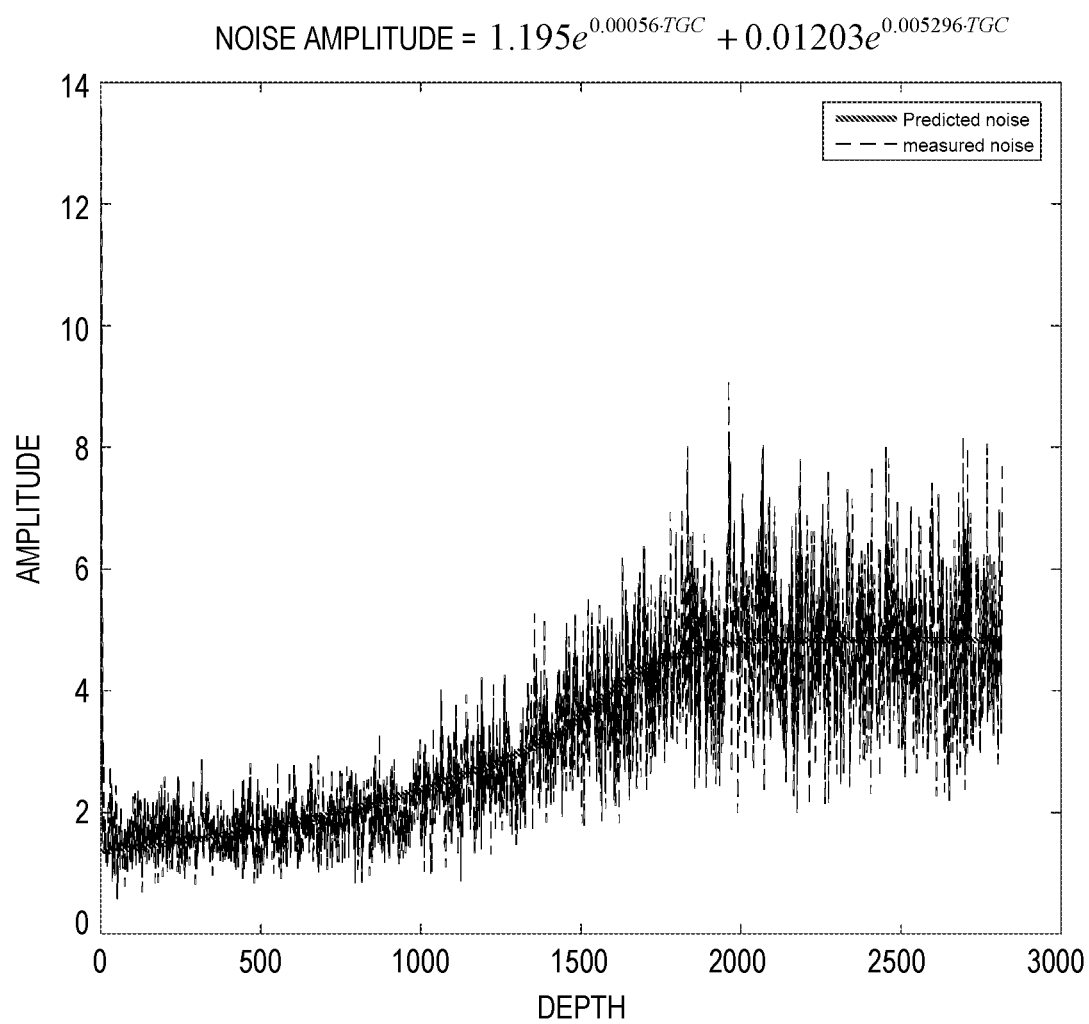
FIG. 13 shows an example of measured noise (dashed lines) and theoretically predicted noise (solid line) of each channel at a given gain setting.

FIG. 13 shows an example of the measured noise (dashed lines) and the theoretically predicted noise (solid line) of each channel at a given gain setting. A final curve fitting provides a sum of two exponentials model with TGC gain as the input (e.g., given any TGC gain the noise amplitude can be predicted). The predicted noise amplitude curve matches well the experimentally measured noise curve along depth.

Figure 14:
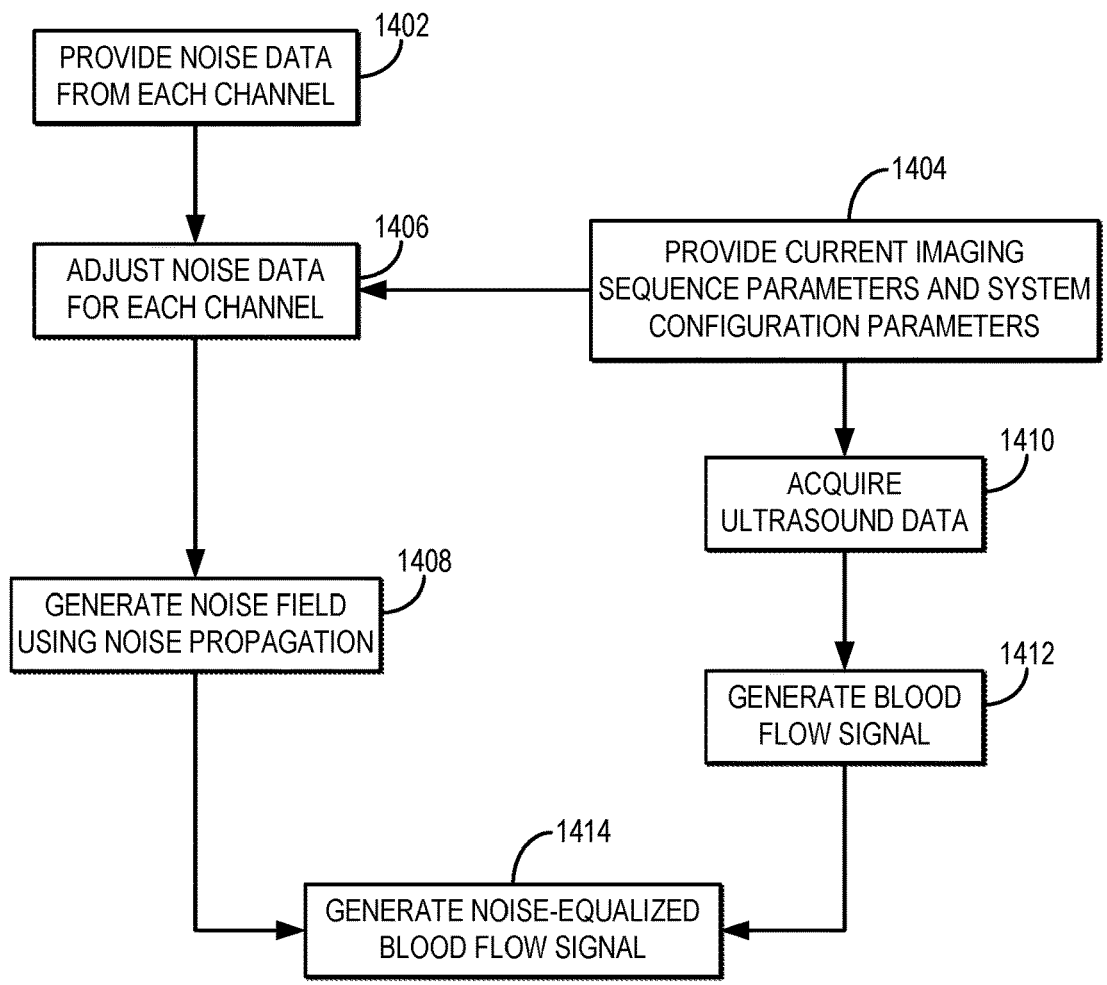
FIG. 14 is a flowchart setting forth the steps of an example method for equalizing a non-uniform noise distribution in a blood flow signal generated from ultrasound data.

Referring now to FIG. 14, a flowchart is illustrated as setting forth the steps of an example method for equalizing a non-uniform noise distribution in a blood flow signal generated from ultrasound data, wherein the noise equalization is implemented using a noise propagation technique. The method includes providing noise data from each transducer element channel to a computer system, as indicated at step 1402. The data can be provided by acquiring the data with an ultrasound imaging system, or by retrieving previously acquired data from data storage. For example, the noise data from each transducer element channel can be measured by turning off the transmission and any gain settings of the ultrasound system. Alternatively a known gain setting with known noise amplitude can be used as well.

The current imaging sequence parameters and system configuration parameters that will be used for imaging the subject are provided to the computer system, as indicated at step 1404. Then at the given imaging sequence and system configurations used for collecting ultrasound data of the targeted tissue, the noise at each channel and each depth is adjusted to reflect the current gain settings of the system (e.g., using the method described above with respect to FIG. 13), as indicated at step 1406. After adjusting the noise amplitude for all the channel data, the noise is propagated through the same beamforming process as the targeted tissue data by the ultrasound system beamformer to generate an estimate of the noise field, as indicated at step 1408. In this process, the noise for each beamformed pixel is obtained by calculating the accumulated noise from all the contributing transducer elements, and the noise amplitude is adjusted by accounting for the processes including spatial compounding, frequency compounding, receive apodization, dynamic receive, receive filtering, signal decoding (if using coded excitation), and so forth.

Ultrasound data acquired using the current imaging sequence and system configuration parameters are provided to the computer system, as indicated at step 1410. The data can be provided by acquiring the data with an ultrasound imaging system, or by retrieving previously acquired data from data storage. The ultrasound data are then processed to generate a blood flow signal (or blood flow image), as indicated at step 1412. For instance, the blood flow signal can be generated using the methods described above.

After the noise field is estimated, it can be used to generate a noise-equalized blood flow signal (or noise-equalized blood flow image), as indicated at step 1414. As one example, the noise-equalized blood flow signal can be generated by dividing the blood flow signal by the noise field. As another example, the noise-equalized signal can be generated by computing a difference between the blood flow signal and the noise field. In some embodiments, the noise field can be processed by a smoothing filter prior to equalization to provide more robust division or subtraction.

Figure 15:
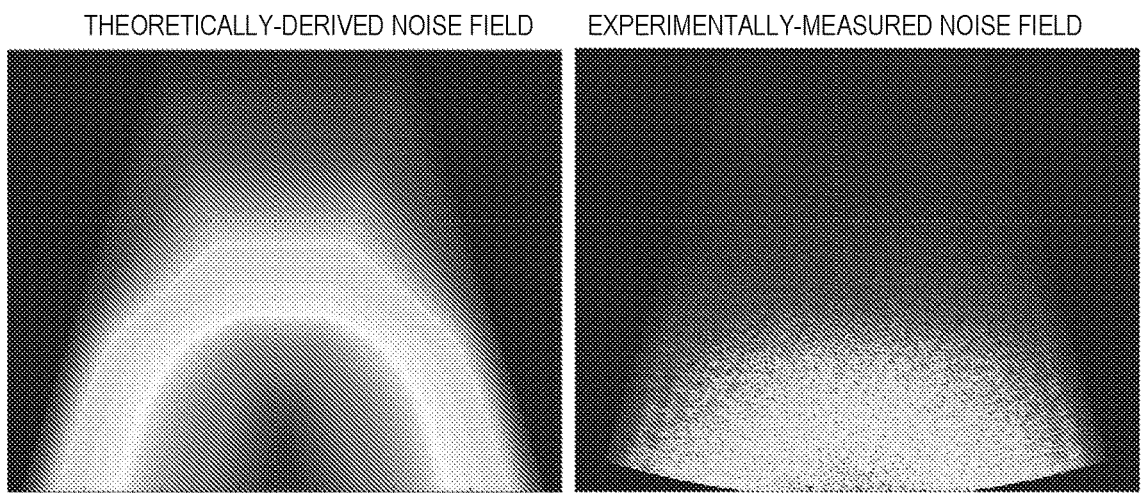
FIG. 15 shows an example of comparing the predicted noise field and the experimentally measured noise field.

Similar to some of the methods described above, the noise propagation-based technique for noise equalization may not account for tissue noise (e.g., noise from tissue attenuation, phase aberration). However, this method does not require collecting new sets of noise data or establishing a database for all the possible imaging settings. The noise for each transducer element only needs to be collected once for each ultrasound system. FIG. 15 shows an example of comparing the predicted noise field and the experimentally measured noise field using the method described here.

An alternative approach to obtain the noise data from each channel is to generate a zero-mean Gaussian-distributed noise data because the noise from each transducer channel is approximately Gaussian-distributed. Because the equalization process can use a normalized noise field (e.g., normalize the derived noise field to the maximum value within the noise field), the amplitude of the noise can be irrelevant. This artificially generated noise data (as opposed to the experimentally measured noise data introduced above) for each channel can be used, followed by the same steps described above with respect to FIG. 14 for the equalization.

Yet another alternative approach to obtain the noise data is to generate a constant matrix (e.g., a matrix with all ones as entries), which imitates the constant variance level of the noise data. Because the equalization process can essentially use the amplitude of the noise (i.e., the variance of the noise data) to equalize the blood flow signal, using a constant matrix can model the variations of the noise amplitude for different system configurations and throughout the beamforming process. This constant matrix for each channel can be used, followed by the same steps described above with respect to FIG. 14 for the equalization.

In another example, non-uniform noise distribution in a blood flow signal can be equalized using an image processing-based equalization method that equalizes the uneven image noise by deriving an equalization field from the blood flow image itself. As shown in FIG. 16, the intensity profile of the original blood flow signal along the depth can be used to calculate a background intensity profile of the blood flow image. A fitted profile of the background intensity can be obtained by curve fitting. As an example, the fitted 1-D intensity profile can be replicated along the lateral dimension to obtain a 2-D noise field, which is then used to equalize the original blood flow signal using the methods described above. An example result is shown in FIG. 16. Multiple intensity profiles can be obtained from the original blood flow signal to obtain a smoother intensity profile for more robust curve fitting. The original blood flow signal can also be smoothed by spatial filters to blur the detailed vasculature signal and derive a background noise field that can be used for equalization. The original blood flow signal can also be decomposed by wavelet processing to extract the low-resolution background intensity profile that can be used for equalization.

The methods described above have great potential for many different clinical applications. As one example, the methods described here can be used for imaging and assessing cancer. For instance, benign and malignant tumors have very different vasculature signatures. The methods described here can noninvasively image and monitor tumor vascularization, which provides critical information for tumor characterization and evaluating treatment response such as response to chemotherapy.

As another example, the methods described here can be used for imaging and assessing inflammation. For instance, hypervascularization generally coincides with inflammatory diseases. The methods described here can be used to image the detailed vasculatures at the pathological site to characterize and quantify inflammation.

As another example, the methods described here can be used for neuroimaging applications. For instance, the superior spatial and temporal resolution provided by the methods described here offer great opportunities to image blood flow in the brain, which is strongly correlated to brain functions and many brain diseases.

As another example, the methods described here can be used for ophthalmological applications. For instance, imaging the fine vessels of the eye is clinically useful. The eye has low ultrasound attenuation and, therefore, very high frequency transducers can be used together with the proposed system to image eye vessels as small as several tens of microns.

As another example, the methods described here can be used for imaging and assessing cardiovascular diseases. For instance, the high temporal resolution offered by the methods described here is advantageous for imaging the high flow speed vessels in the cardiovascular system. The high spatial resolution has potential to image the coronary arteries.

The present disclosure has described one or more preferred embodiments, and it should be appreciated that many equivalents, alternatives, variations, and modifications, aside from those expressly stated, are possible and within the scope of the invention.

The invention claimed is:

1. A method for generating an image that depicts blood flow in a subject's vasculature using an ultrasound imaging system, the steps of the method comprising:
    (a) acquiring ultrasound signal data from a field-of-view in a subject;
    (b) dividing the acquired ultrasound data into a plurality of ultrasound data submatrices each corresponding to a subvolume of the field-of-view, wherein each ultrasound data submatrix has at least one matrix dimension that is smaller than a corresponding matrix dimension of the ultrasound signal data;
    (c) performing a low-rank matrix decomposition on each ultrasound data submatrix, thereby generating decomposed data that includes decomposed matrix values for each ultrasound data submatrix;
    (d) estimating at least one of a low-order cutoff value based on the decomposed data or a high-order cutoff value based on the decomposed data, wherein the low-order cutoff value differentiates signals attributable to tissue from signals attributable to blood flow and the high-order cutoff value differentiates signals attributable to blood flow from signal attributable to noise;
    (e) extracting signals that are attributable to blood flow in the subject's vasculature from each ultrasound data submatrix using the at least one of the low-order cutoff value or high-order cutoff value; and
    (f) combining the extracted signals to generate an image that depicts blood flow in the subject's vasculature in the field-of-view.

2. The method as recited in claim 1, wherein step (c) includes performing a singular value decomposition such that the decomposed matrix values are singular values and the decomposition data also includes singular vectors.

3. The method as recited in claim 2, wherein step (d) includes generating a singular value curve by plotting the singular values and selecting the low-order cutoff value based on a decay rate of singular value curve.

4. The method as recited in claim 3, wherein the decay rate of the plotted singular values is computed using one of a gradient calculation method or a fitting method.

5. The method as recited in claim 2, wherein step (d) includes generating a singular vector frequency curve based on the singular vectors and selecting the low-order cutoff value based on a predetermined frequency cutoff value.

6. The method as recited in claim 5, wherein the singular vector frequency curve is computed based on estimating a mean Doppler frequency for each singular vector.

7. The method as recited in claim 2, wherein step (d) includes generating a singular value curve by plotting the singular values and selecting the high-order cutoff value based on a linear fitting of higher-order singular values in the singular value curve.

8. The method as recited in claim 7, wherein the high-order cutoff value is selected as a point in the singular value curve at which the linear fitting begins to deviate from the singular value curve by a threshold amount.

9. The method as recited in claim 2, wherein step (d) includes generating a singular vector frequency curve based on the singular vectors and selecting the high-order cutoff value based on a linear fitting of singular vector frequency values in a transition region between lower-order singular vector frequency values and higher-order singular vector frequency values.

10. The method as recited in claim 9, wherein the high-order cutoff value is selected as a point in the singular vector frequency curve at which the linear fitting deviates from the singular vector frequency curve transition region near the lower-order singular vector frequency values by a threshold amount.

11. The method as recited in claim 1, wherein step (c) includes performing an eigenvalue decomposition such that the decomposed matrix values are eigenvalues and the decomposition data also includes eigenvectors.

12. The method as recited in claim 1, wherein step (e) includes weighting the decomposed matrix values in the decomposed data that are lower than the low-order cutoff value and higher than the high-order cutoff value using weighting coefficients to reduce contributions from those decomposed matrix values in the data submatrices.

13. The method as recited in claim 12, wherein the weighting coefficients include zero-valued coefficients.

14. The method as recited in claim 12, wherein step (e) includes performing an inverse of the low-rank matrix decomposition to convert the decomposed data to estimates of blood flow signal in each data submatrix.

15. The method as recited in claim 1, wherein step (f) includes generating image intensity values at each pixel location in the image by averaging the extracted signals at a given pixel location across a plurality of local windows that contain the given pixel.

16. The method as recited in claim 1, wherein at least some of the ultrasound data submatrices correspond to overlapping subvolumes.

17. The method as recited in claim 1, wherein at least some of the ultrasound data submatrices are sized different from others of the ultrasound data submatrices.

18. The method as recited in claim 1, wherein step (f) includes denoising the extracted signals using a temporal denoising filter based on a temporal behavior of the extracted signals.

19. The method as recited in claim 18, wherein the denoising filter includes a high-pass filter component to remove low frequency components attributable to residual energy in a low frequency spectrum not associated with blood signal.

20. The method as recited in claim 18, wherein the denoising filter is based on symmetric temporal frequency spectrum characteristics of noise signals and asymmetric temporal frequency spectrum characteristics of blood signals.

21. The method as recited in claim 20, wherein the symmetric temporal frequency spectrum characteristics are determined based on at least one of a sum of an absolute difference, a cross-correlation, or a shape similarity measurement.

22. The method as recited in claim 1, wherein step (d) includes validating the at least one of the low-order cutoff value or the high-order cutoff value based on a set of rules related to a fidelity of the at least one of the low-order cutoff value or the high-order cutoff value.

23. The method as recited in claim 22, wherein the set of rules includes at least one of:
 (i) rejecting a high-order cutoff value when a low-order cutoff value is greater than the high-order cutoff value;
 (ii) rejecting at least one of a low-order cutoff value or a high-order cutoff value when a difference between the low-order cutoff value and the high-order cutoff value is less than a threshold value; or
 (iii) rejecting at least one of a low-order cutoff value or a high-order cutoff value when a difference between the low-order cutoff value and the high-order cutoff value is greater than a threshold value.

24. The method as recited in claim 1, wherein the subject's vasculature in the field-of-view includes at least one of small blood vessels or microvasculature.

25. A method for generating an image that depicts blood flow in a subject's vasculature using an ultrasound imaging system, the steps of the method comprising:
 (a) acquiring ultrasound signal data from a field-of-view in a subject and dividing the acquired ultrasound data into a plurality of ultrasound data submatrices each corresponding to a subvolume of the field-of-view and each submatrix having at least one matrix dimension that is smaller than a corresponding matrix dimension of the ultrasound signal data;
 (b) performing a low-rank matrix decomposition on the ultrasound data submatrices, thereby generating decomposed data that includes decomposed matrix values for the ultrasound data;
 (c) estimating a low-order cutoff value based on the decomposed data and a high-order cutoff value based on the decomposed data, wherein the low-order cutoff value differentiates signals attributable to tissue from signals attributable to blood flow and the high-order cutoff value differentiates signals attributable to blood flow from signal attributable to noise;
 (d) extracting signals that are attributable to blood flow in the subject's vasculature from the ultrasound data using the at least one of the low-order cutoff value or high-order cutoff value; and
 (e) generating an image that depicts blood flow in the subject's vasculature in the field-of-view based on the extracted signals.

26. The method as recited in claim 25, wherein step (e) includes processing the image with a computer system to reduce effects of non-uniform noise distribution in the image.

27. The method as recited in claim 26, wherein processing the image to reduce effects of non-uniform noise distribution in step (e) includes providing to the computer system, a noise profile that estimates background noise in the field-of-view, and further includes reducing effects of unequal noise distribution in the generated image with the computer system using the noise profile.

28. The method as recited in claim 25, wherein step (e) includes providing to the computer system, a noise profile that estimates background noise in the field-of-view, and wherein the noise profile is used to create a spatially weighted data fidelity term that is used in a model-based image reconstruction to generate the image.

* * * * *